(12) United States Patent
Giunta et al.

(10) Patent No.: US 8,748,195 B2
(45) Date of Patent: Jun. 10, 2014

(54) MOLECULAR MARKERS FOR URINARY TRACT INFECTIONS

(75) Inventors: Francesco Giunta, Pisa (IT); Francesco Forfori, Pisa (IT); Giada Seri, Pisa (IT)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 0 days.

(21) Appl. No.: 13/635,521

(22) PCT Filed: Mar. 15, 2011

(86) PCT No.: PCT/IB2011/051073
§ 371 (c)(1),
(2), (4) Date: Dec. 13, 2012

(87) PCT Pub. No.: WO2011/114287
PCT Pub. Date: Sep. 22, 2011

(65) Prior Publication Data
US 2013/0084650 A1      Apr. 4, 2013

(30) Foreign Application Priority Data
Mar. 18, 2010  (IT) .............................. RM2010A0121

(51) Int. Cl.
G01N 33/74   (2006.01)
G01N 33/58   (2006.01)
G01N 33/53   (2006.01)

(52) U.S. Cl.
USPC ........................................... 436/501; 435/7.1

(58) Field of Classification Search
CPC combination set(s) only.
See application file for complete search history.

(56) References Cited

U.S. PATENT DOCUMENTS

| 2010/0056763 A1 | 3/2010 | Bergmann et al. |
| 2013/0096052 A1 * | 4/2013 | Struck et al. .................... 514/2.9 |

FOREIGN PATENT DOCUMENTS

| WO | WO 2008/104321 | * | 2/2009 | ............. G01N 33/74 |
| WO | WO2011/110565 | * | 9/2011 | ............. G01N 33/569 |

OTHER PUBLICATIONS

Meisner et al., Eur J. Anaesthesiol, 2001; 18(2):79-87, Abstract only.*
Morgenthaler et al., Clinical Chem 2002; 48, No. 5, pp. 788-790.*
Hooton et al., (Urinary Catheter Guidelines CID; 2010:50).*
Brams GmbH catalog, 1998-2012 retrieved from http://www.procalcitonin.com/default.aspx?tree=_2_4%)/0D).*
Chiapinni et al.,(Crit Care 1998; 2(Suppl 1:P038).*
Ayazi, P. et al., "Comparison of procalcitonin and C-reactive protein test in children with urinary tract infection," Iranian Journal of Pediatrics, 2009, vol. 19, No. 4, pp. 381-386.
Gendrel, D. et al., "Procalcitonin and prediction of vesico-ureteral reflux in pediatric urinary tract infection," Bull. Acad. Natl. Med., Nov. 2007, vol. 191, No. 8, pp. 1731-1743.
English Abstract of Gendrel, D. et al., "Procalcitonin and prediction of vesico-ureteral reflux in pediatric urinary tract infection," Bull. Acad. Natl. Med., Nov. 2007, vol. 191, No. 8, pp. 1731-1743.
Gendrel, D., "Urinary tract infection and biological markers: C-reactive Protein, interleukins and procalcitonin," Arch Pediatr, 1998, vol. 5 Suppl. 3, pp. 2269S-2273S.
English Abstract of Gendrel, D., "Urinary tract infection and biological markers: C-reactive Protein, interleukins and procalcitonin," Arch Pediatr, 1998, vol. 5 Suppl. 3, pp. 2269S-2273S.
International Search Report for PCT/IB2011/051073 dated Sep. 23, 2011.
Kotoula, a. et al., "Comparative efficacies of procalcitonin and conventional inflammatory markers for prediction of renal parenchylmal inflammation in pediatric first urinary tract infection," Urology, Apr. 2009, vol. 73, No. 4, pp. 782-786.
Lai, C. C. et al., "Diagnostic value of procalcitonin for bacterial infection in elderly patients in the emergency department," J. Am. Geriatr. Soc., Mar. 2010, vol. 58, No. 3, pp. 518-522.
Leroy, S. et al. "Procalcitonin to reduce the number of unnecessary cystographies in children with a urinary tract infection: a European validation study," J. Pediatr., Jan. 2007, vol. 150, No. 1, pp. 89-95.
Leroy, S. et al., "Procalcitonin as a predictor of vesicoureteral reflux in children with a first febrile urinary tract infection," Pediatrics, 2005, vol. 115, pp. E706-E709.
Nanda, N. et al., "Novel Biomarkers for the Diagnosis of Urinary Tract Infection—A systematic Review," Biomarker Insights, 2008, vol. 4, pp. 111-121.
Van Rossum, A. M. et al., "Procalcitonin as an early marker of infection in neonates and children," Lancet Infect. Dis., Oct. 2004, vol. 4, No. 10, pp. 620-630.

* cited by examiner

*Primary Examiner* — Shafiqul Haq
*Assistant Examiner* — Carmencita M Belei
(74) *Attorney, Agent, or Firm* — Millen, White, Zelano, Branigan, P.C.

(57) ABSTRACT

The invention relates to an in vitro method for determining procalcitonin levels in plasma and urine as a diagnostic marker to identify patients with urinary tract infections, in vitro methods to perform said determination, a kit for the diagnosis of patients with urinary tract infections, and the usefulness of procalcitonin in the diagnosis urinary tract infections.

6 Claims, 2 Drawing Sheets

MOLECULAR MARKERS FOR URINARY TRACT INFECTIONS

Figure 1:
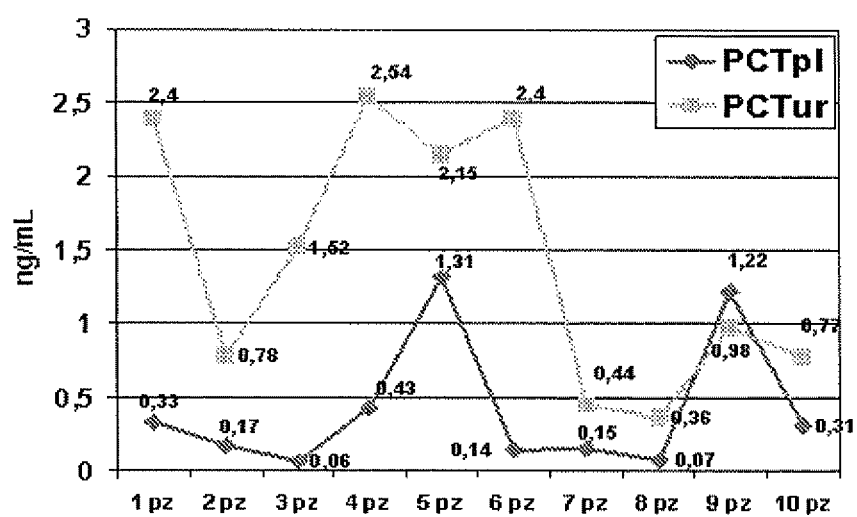

The invention relates to an in vitro method for determining procalcitonin levels in plasma and urine as a diagnostic marker to identify patients with urinary tract infections, in vitro methods to perform said determination, a kit for the diagnosis of patients with urinary tract infections, and the usefulness of procalcitonin in the diagnosis urinary tract infections.

PRIOR ART

Urinary tract infections (UTIs) are a very common problem, often associated with the use of a urinary catheter (Hooton T M et al. Clin Infect Dis. 2010 Mar. 1, 50 (5):625-63) and are normally caused by saprophytic bacteria in the intestine and external genitalia, and less commonly, by fungi and viruses. These organisms, under certain conditions, can colonize the urinary tracts until reaching the bladder, via the urethra. Clinically, urinary infection presents with fever, dysuria, strangury, urinary frequency, urinary urgency and moderate lower back pain.

The clinical symptoms are not always sufficient to provide a diagnosis, especially in intensive care units, where patients are often unable to communicate their symptoms and various comorbidities can often mask the precise origin of the infection.

Laboratory tests are therefore required, both to isolate the pathogens involved and to assess any complications and identify specific treatments.

The technique of choice for diagnosing urinary tract infections is represented by the urine culture. This test allows to isolate the bacterium responsible for the infection and to assess the sensitivity or resistance to antibiotics by means of an antibiogram. The time taken to obtain the urine culture results varies from 24 to 48 hours depending on the microbial species involved.

Pending the results, empirical treatment based solely on clinical observation is often performed, which can lead to inappropriate use of antibiotic therapy and patients with completely unnecessary (negative) urine cultures.

Consequently, the need to identify new tools for the early diagnosis of UTI, capable of predicting possible complications and improving the outcome, especially in certain "difficult" situations such as critically ill neonates or patients, was of paramount importance.

SUMMARY OF THE INVENTION

The invention relates to an in vitro method and a kit for the diagnosis and/or monitoring of urinary tract infections. The invention described herein is based on the discovery that the concentration of procalcitonin in the urine samples of patients has a predictive value for the diagnosis of urinary tract infections. In addition, the inventors have also observed that in patients with urinary tract infections, the concentration of procalcitonin in the urine is greater than the plasma concentration of procalcitonin, while in patients unaffected by urinary tract infection the concentration of procalcitonin in the urine is lower than the plasma concentration of procalcitonin. The determination of the procalcitonin concentration in urine can be used to diagnose the presence of urinary tract infection either by comparing the value of the concentration in the urine of patients with standard values and/or according to the relationship between the concentration of plasma procalcitonin and the concentration of procalcitonin in the urine.

Therefore, the subject of the present invention is an in vitro method for diagnosing and/or monitoring urinary tract infections, including a stage in which the concentration of procalcitonin in the urine sample of a patient is determined.

The subject of the invention is also the above-mentioned method further including a stage in which the concentration of the plasma procalcitonin of said patient is also determined.

The subject of the invention is also a kit for the diagnosis and/or monitoring and/or assessment of the severity in vitro of urinary tract infections, including aliquots of reagents necessary for determining the concentration of procalcitonin in a urine sample and optionally a plasma sample.

The subject of the invention is also the use of procalcitonin for diagnosis and/or monitoring of urinary tract infections.

The present invention has the advantage of being able to diagnose and/or monitor a patient with a urinary tract infection using a very simple, non-invasive method as well as a faster method than those used in the technique known as urine culture.

The advantages, characteristics and methods of use of the present invention are evident from the following detailed description of certain embodiments, presented as an example and without limitation.

DETAILED DESCRIPTION OF THE FIGURES

FIG. 1. Population with positive urine culture. This figure shows the values of PCTur (urinary procalcitonin) and PCTpl (plasma procalcitonin) of 10 patients with urinary tract infections.

Figure 2:
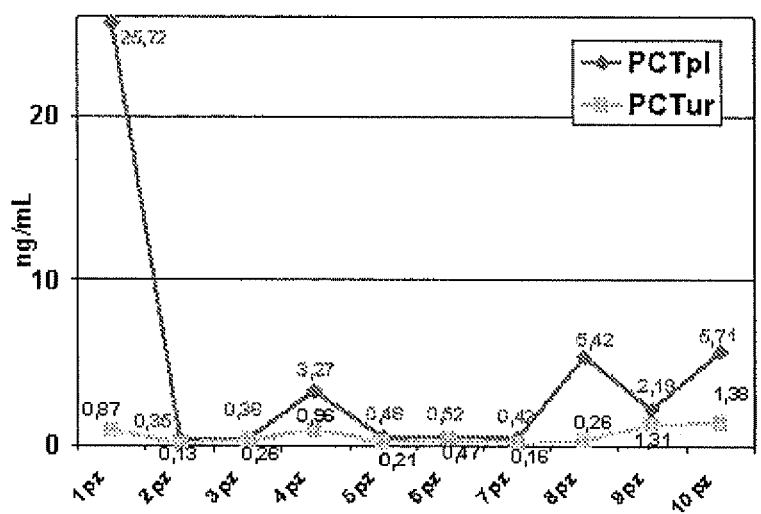

FIG. 2. Population with negative urine culture. This figure shows the values of PCTur (urinary procalcitonin) PCTpl (plasma procalcitonin) of 10 patients without urinary tract infections.

FIGS. 1 and 2 show that the PCTur values are greater than the PCTpl values in 9 out of 10 cases in the population with positive urine culture and in no patients belonging to the population with negative urine culture.

DETAILED DESCRIPTION OF THE INVENTION

The present description provides an in vitro method for the diagnosis and/or monitoring of urinary tract infections. The method according to the invention makes it possible to diagnose and/or monitor urinary tract infections. The method according to the invention makes it possible to diagnose the presence or absence of urinary tract infections, to assess (diagnose) the severity of the infection with regard to a single determination (i.e. the higher the concentration of procalcitonin, the more severe the infection, risk stratification at the first determination) and to monitor the progress of the infection during treatment of the infection.

The term "urinary tract infection" in the present description means the invasion of the urinary tract, which is normally sterile, by germs (bacteria, fungi and/or viruses) in quantities such as to determine the inflammatory response of the urothelium.

Examples of microorganisms that can cause urinary tract infections are *E. Coli, Proteus Mirabilis, E. Faecalis, Saprophyticus, Staphylococcus, Enterococcus, Klebsiella, Pseudomonas, Candida albicans*, etc. Epidemiological data indicate that in one third of cases, urinary tract infections are associated with the use of a urinary catheter. The present invention can be applied both to patients wearing permanent or temporary urinary medical devices (catheters, nephrostomy, cystostomy) and to patients of all ages without these devices.

The method according to the invention includes a stage in which the concentration of procalcitonin in the urine sample of a patient is determined. Procalcitonin (PCT) is the precursor of calcitonin, a hormone responsible for the homeostasis of calcium produced by the medullary neuroendocrine C-cells of the thyroid.

Advantageously, the method of the invention includes a further stage during which the concentration of procalcitonin in a plasma sample of said patient is also determined. The determination of procalcitonin not only in urine but also in plasma can more accurately diagnose the presence or absence of urinary tract infection in patients whose urine and plasma has been analysed. The clinical study carried out by the inventors has, in fact, shown that in all patients with urinary tract infections the value of procalcitonin in the urine is greater than in the plasma, whereas this value is lower in negative patients. This embodiment can be used, for example, in patients whose urinary procalcitonin values are not sufficient to give a certain indication of the presence or absence of urinary tract infection or in patients presenting a complex clinical picture (for example the possible presence of both urinary tract infection and systemic infection).

In general, to determine the concentration of procalcitonin in the urine and/or plasma, any method well-known to experts in the sector, which allows for determining the concentration of procalcitonin in a biological fluid may be considered suitable for the purposes of this description. For example, quantitative and semi-quantitative commercial immunoassays such as LUMItest® PCT chemiluminescence, LIAISON® BRAHMS PCT®, TRACE: KRYPTOR®, BRAHMS PCT, PCT®-Q. The assay conditions may be modified to avoid potential interferences caused by components of the urine matrix.

The concentration of procalcitonin in the urine and/or plasma sample to be tested will be determined by incubating the sample, at suitable temperatures and for suitable amounts of time, with a primary antibody specific for procalcitonin, suspended in appropriate concentrations in a suitable buffer. The term antibody in this description refers to a whole antibody or a fragment of an antibody; an antibody fragment includes, but is not limited to fragments $F(ab')_2$ and Fab' or single chain antibodies.

For the purposes of this description, the term "primary antibody specific for procalcitonin" refers to any antibody capable of selectively binding to any portion of procalcitonin.

The development of selective antibodies for a particular protein is now carried out using conventional techniques, taught in laboratory manuals, and is also provided as a service by numerous companies. It will therefore not be necessary in this description to provide further details on the creation of antibodies that can also be ordered from suitable companies.

Therefore, to create a primary antibody specific for procalcitonin, any standard technique will be sufficient for the development of both polyclonal and monoclonal antibodies. In addition, antibodies specific for procalcitonin are also available on the market (e.g. commercial antibodies, which may be used are the commercial antibodies by the company Abcam with codes ab53897 (rabbit polyclonal), ab90489 (mouse monoclonal), ab24454 (HRP conjugated mouse monoclonal), ab14817 (HRP conjugated mouse monoclonal)) and can be used for the purposes of the present invention without further details being provided in this description. The details of primary antibody incubation protocols are well known to technicians in the sector and, if using commercial antibodies, the details are given in the supplier's instructions. These incubation protocols include the use of appropriate buffers, such as PBS (phosphate buffer saline) or if using commercial antibodies, buffers specifically recommended by the manufacturer.

In order to detect the primary antibody, it can be marked with any compound commonly used in the labelling of antibodies and a fluorophore may be used in a particular, chosen in the group consisting of: hydroxycoumarin, aminocoumarin, methoxycoumarin, europium, samarium, FITC, Cy3, Cy5, Cy2, Cy7, XL665 or an enzyme such as alkaline phosphatase or peroxidase.

Alternatively, if a primary antibody is used, which is not directly labelled, the primary antibody can be detected by the use of any labelled secondary antibody, which selectively recognizes said primary antibody. As is known in the literature, a secondary antibody is specific for the constant region, also known as the Fc portion, of the primary antibody, which in turn is dependent on the type of animal used for the development of the primary antibody itself. In other words, it is the type of animal used for immunization with the epitope involved (primary antibody) which defines the nature of the secondary antibody, so, for example, if the primary antibody is obtained from a rabbit, the secondary will be anti-rabbit; if the animal immunized is a sheep, the secondary antibody will be anti-sheep, if the primary antibody is developed in a mouse, the secondary antibody will be an anti-mouse secondary antibody, etc.

The secondary antibody can be labelled with any compound commonly used in the labelling of antibodies and a fluorophore may be used in a particular, chosen in the group consisting of: hydroxycoumarin, aminocoumarin, methoxycoumarin, europium, samarium, FITC, Cy3, Cy5, Cy2, Cy7, XL665 or an enzyme such as alkaline phosphatase or peroxidase.

In one embodiment the concentration of procalcitonin can be determined using an anti-procalcitonin primary antibody, for example, a polyclonal antibody conjugated to a fluorescent marker such as europium and an anti-procalcitonin secondary antibody, which recognizes an epitope different from the one recognised by the primary antibody, such as a monoclonal antibody conjugated to a fluorescent marker such as XL665.

The method of the invention can be performed manually by or using any instrument known to technicians in the sector capable of automatically performing said method, for example, laboratory instruments such as Kryptor BRAHMS, or other methods used for determination of plasma procalcitonin (e.g. LUMItest® PCT-LIAISON®, BRAHMS PCT®-Q) may be used.

In one embodiment the value of procalcitonin concentration in the urine is compared to one or more values that indicate the presence or absence of urinary tract infections, for which a concentration less than 0.05 ng/mL is predictive of the absence of urinary tract infection and/or a concentration greater than 0.3 ng/mL is predictive of the presence of urinary tract infection.

In one embodiment the method of the invention may include an additional step in which the value of procalcitonin concentration in urine is compared with the value of procalcitonin concentration in plasma, for which a relationship between the concentration of procalcitonin in the urine and procalcitonin in the plasma greater than 1 is predictive of the presence of urinary tract infection.

The subject of the present invention is also a kit for the diagnosis and/or prognosis in vitro of urinary tract infections, including aliquots of reagents necessary for determining the concentration of procalcitonin in a urine sample and optionally a plasma sample.

For the first time, therefore, a rapid instrument has been provided, which can be used to identify patients who have urinary infections and/or to monitor the course of infection in view of a specific treatment protocol.

In its simplest form the kit will contain one or more aliquots of a specific anti-calcitonin antibody and an accompanying leaflet, for example, containing instructions for the interpretation of diagnostic results, and optionally means to collect and store the urine and/or plasma sample. For the purposes of this description any antibody that can selectively bind to procalcitonin can be included in the kit claimed herein. In particular, the kit may contain one or more anti-procalcitonin antibody, each developed, for example, for a different epitope of the protein and the antibody will possibly be able to be conjugated to common antibody markers such as fluorophores or enzymes. The kit may, where appropriate, include the use of monoclonal and/or polyclonal anti-procalcitonin antibodies on the market. The kit may also contain accompanying leaflets. These leaflets may indicate the components of the kit and the recommended protocol. In addition, the instructions may also contain information regarding the interpretation of the value of procalcitonin obtained for the urine and plasma samples analysed, and in particular, as already stated a urinary procalcitonin concentration of less than 0.05 ng/mL is predictive of the absence of urinary tract infection, a concentration greater than 0.3 ng/mL is predictive of the presence of urinary tract infection, and a PCTur/PCTpl relationship >1 is predictive of the presence of urinary tract infection where PCTur is the urinary procalcitonin of the patient and PCTpl is the plasma procalcitonin.

The kit may also contain one or more aliquots of a secondary antibody, specific for the primary antibody. The secondary antibody, as is known to technicians in the sector and as noted above, must be able to specifically recognize the constant portion of the primary antibody used; therefore the choice of secondary antibody to use will depend on the animal immunized with the epitope concerned. The secondary antibody can be labelled with any compound commonly used in the labelling of antibodies.

The kit may also contain one or more aliquots of negative and/or positive controls.

A negative control signifies any urine or plasma sample of a patient who does not have a urinary tract infection. In one particular embodiment, the negative control may be represented by a urine sample with a procalcitonin concentration of less than 0.05 ng/mL.

The positive control will allow for testing the correctness of the procedure performed and the possible validity of the methods used since it may contain the plasma or urine sample of a patient with a urinary tract infection. In particular, the positive control, most suitable but not limited to this invention, will be a urine sample with a procalcitonin concentration of more than 0.3 ng/mL.

The kit may also contain one or more aliquots of reagents for the detection of procalcitonin in the urine and/or plasma. These reagents consist of any solution useful for the conduction of the various steps leading to the identification of the value of procalcitonin concentration in the sample analysed. In particular, buffer solutions may be used, for example and without limitation, PBS (phosphate buffer saline); a blocking solution such as PBS supplemented with bovine serum albumin. The subject of the invention is also the use of procalcitonin in the diagnosis, monitoring and evaluation of the severity of urinary tract infections, such as infections associated with the use of a urinary catheter.

Reported below are the experimental results and examples intended to illustrate the reports contained in this description: these examples must not be considered as a limitation of the above description and the subsequent claims.

Description of the Population used in a Clinical Study of Patients with Suspected Urinary Tract Infection.

Patients admitted to the ICU with suspected urinary tract infection were recruited in a clinical study. Each patient was simultaneously subjected to the following tests:

standard urinalysis (chemical and physical examination) and urine culture;

plasma PCT;

urinary PCT.

On the basis of urine culture results 10 subjects with positive urine culture and 10 subjects with negative urine culture were enrolled.

A total of 20 patients (9 females and 11 males) with an average age of 70 years were enrolled. The age of the patients selected varied from 33 to 91 years.

Each patient had to present at least one of the following inclusion criteria:

Fever or hypothermia;

Leukocytosis/leukopenia;

Lower back pain and/or dysuria;

Other inexplicable signs of SIRS;

FUO;

Recurrent UTI.

The exclusion criteria included:

1. oliguria/anuria;
2. presence of ureterosigmoidostomy;
3. renal abnormalities preventing an adequate urine sample;
4. Liver failure.

The urine culture is considered positive if there is a development of $10^5$ CFU/mL for no more than two microorganisms (polymicrobial etiology in 14-30% of cases). In the case of *Candida* spp. the significance threshold was considered as $10^4$ CFU/mL. Also for Gram positives (especially coagulase-negative enterococci and staphylococci) and in the case of antimicrobial treatment there is a tendency to consider a count of less than $10^5$ CFU/mL as significant.

Results of the Clinical Study

The population with positive urine culture was shown to have a higher urinary PCT than plasma PCT in 9 out of 10 cases (FIG. 1).

The mean urinary PCT value was 1.4 ng/mL while the mean plasma PCT value was 0.4 ng/mL. Urinary PCT ranged between 0.36 and 2.54 ng/mL while plasma PCT ranged between 0.06 and 1.22 ng/mL.

The median urinary PCT value was 1.25 ng/mL and the median plasma PCT value was 0.24 ng/mL.

The relationship between urinary PCT and plasma PCT had a value between 0.8 and 25.33 ng/mL, a mean value of 7.32 ng/mL and a median value of 4.86 ng/mL.

The average temperature of the subjects was 37.02° C. with 1 patient who had a temperature <35° C., 3 patients ≥36° C. and <37° C., 4 patients ≥37° C. and <38° C. and ≥2 patients 38 ° C.

The value of white blood cells (nv 4.50 to $10.00 \times 10^3/\mu L$) ranged between 5.37 and $22.12 \times 10^3/\mu L$ with a mean of $12.22 \times 10^3/\mu L$ and a median of $11.55 \times 10^3/\mu L$.

The percentage of neutrophils (nv 40.0 to 75.0%) ranged from 67.3 to 88.4% with a mean of 78.8%.

The subjects' creatinine (nv 0.50 to 0.90 mg/dL) ranged from a minimum of 0.3 to a maximum of 2.85 mg/dL with a mean of 0.78 mg/dL.

To calculate the value of creatinine clearance the following Cockcroft-Gault formula was used:

males [(140−age)×body weight (kg)/(serum creatinine×72)]

females [(140−age)×body weight (kg)×0.85/(serum creatinine×72)].

In the study subjects, clearance ranged from 27 to 226.8 ml/min with a mean of 129.16 ml/min and a median of 115.4 ml/min.

The population with negative urine culture was shown to have a lower urinary PCT than plasma PCT in all patients.

The mean urinary PCT value was 0.6 ng/mL while the mean plasma PCT value was 4.44 ng/mL. Urinary PCT ranged between 0.13 and 1.38 ng/mL while plasma PCT ranged between 0.35 and 25.72 ng/mL.

The median urinary PCT value was 0.36 ng/mL and the median plasma PCT value was 1.36 ng/mL.

The relationship between urinary PCT and plasma PCT had a value between 0.03 and 0.9 ng/mL, a mean value of 0.40 ng/mL and a median value of 0.37 ng/mL.

The average temperature of the subjects was 37.7° C. with 1 patient who had a temperature ≥36° C. and <37° C., 1 patient ≥37° C. and <38 ° C., and 8 patients ≥38° C.

The value of white blood cells ranged between 4.27 and $39.2 \times 10^3/\mu L$ with a mean of $12.86 \times 10^3/\mu L$ and a median of $8.61 \times 10^3/\mu L$.

The percentage of neutrophils ranged between 65.5 and 93.9% with a mean of 85.5%.

The creatinine of the subjects ranged from a minimum of 0.55 to a maximum of 1.61 mg/dL with a mean of 0.97 mg/dL.

Using the Cockcroft-Gault formula, the creatinine clearance ranged from 38.4 to 169.4 ml/min with a mean of 78.72 ml/min and a median of 76.1 ml/min.

In the population of patients with negative urine culture PCTur values lower than PCTpl values were observed in all 10 patients in the population with negative urine culture and in only 1 case in the population with positive urine culture. (FIG. 1) The latter patient was the only subject enrolled to have severe renal dysfunction demonstrated by the creatinine clearance value of 27 ml/min, estimated using the Cockcroft-Gault formula. It is therefore possible that in the subject with severe renal dysfunction, PCT has accumulated in the plasma, without proper excretion in the urine, and this has led to a PCTpl value greater than the PCTur value despite the positive culture.

In the population with positive urine culture the median of the PCTur values was 1.25 ng/mL while in the population with negative urine culture this value was 0.36 ng/mL, indicating a clear differentiation between the two groups.

The median values of PCTpl also show a significant difference: 5 in the population with positive urine culture its value (0.24 ng/mL) indicates that the majority of subjects do not have any other infection; whereas in the population with negative urine culture its value (1.36 ng/mL) indicates that the majority of patients have a bacterial infection. (FIG. 2 ).

To evaluate, whether the accuracy of measurement of PCT was affected by the use of urine as sample matrix, five urine and serum samples each of healthy individuals with non-detectable PCT were spiked with recombinant PCT and measured in the KRYPTOR PCT Assay. The recovery of PCT in urine was 20-30% lower than in serum. Thus, the extent of reduced recovery in urine is relatively small, and the conclusions drawn above all hold, even if recovery in urine and serum have not been identical. The urine PCT values determined in the clinical samples of the present invention can be corrected by multiplying them with 1.25 to account for the reduced recovery in urine matrix.

Statistical Analysis

The data extrapolated from the results of the clinical study were subjected to statistical analysis to assess whether the PCTur/PCTpl ratio >1 would be able to diagnose urinary tract infection with sensitivity and specificity.

|  | Patients with infection | Patients without infection | Total |
| --- | --- | --- | --- |
| Test+ | A | b | A + b |
| Test− | C | d | C + d |
| Total | A + c | B + d | |

|  | Patients with infection | Patients without infection | Total |
| --- | --- | --- | --- |
| Test+ | 9 | 0 | 9 |
| Test− | 1 | 10 | 11 |
| Total | 10 | 10 | 20 |

Sensitivity is the probability that an infected patient is positive to the test and in our case Sensitivity=$a/a+c$=9/(9+1)=0.9 i.e. 90%.

Specificity, on the other hand, is the probability that a healthy subject is negative to the test and in our case:

Specificity=$d/b+d$=10/(0+10)=1 i.e. 100%

We can also calculate the positive predictive value (PPV), which corresponds to the proportion of subjects with positive tests who have the infection and are therefore correctly diagnosed as infected:

$PPV=a/a+b$=9/(9+0)=1 i.e. 100%.

EXAMPLE 1

Measuring Plasma Procalcitonin

The blood sample for analysis is collected from the patient using the BRAHMS PCT sensitive KRYPTOR, a kit designed for doses of procalcitonin in automated immunofluorescence assays on human serum or plasma samples (EDTA, heparin). This quantitative method uses a sheep anti-procalcitonin polyclonal antibody conjugated to a fluorescent marker, europium cryptate and other substances such as a buffer including bovine albumin, non-immunized mouse immunoglobulin and potassium fluoride; a monoclonal mouse anti-catacalcin antibody also conjugated to a fluorescent marker XL665 and with buffer, bovine albumin, mouse immunoglobulin, potassium fluoride; and finally, ready for use, a diluent formed of human serum, Kathon, EDTA is available.

The measurement of PCT in this assay is based on TRACE technology (Time-Resolved Amplified scramble Emission), which measures the signal emitted from an immunocomplex with time delay. The sample is excited with a nitrogen laser at 337 nm and the donor (cryptate) emits a long-life fluorescent signal in the millisecond range at 620 nm, while the acceptor (XL 665) generates a short-life signal in the range of nanoseconds to 665 nm. If an immunocomplex is formed, both the signal amplification and the prolonged lifespan of the acceptor signal occur at 665 nm, and the signal can be measured in microseconds.

The PCT molecules are sandwiched between the two antibodies and by measuring the length of the signal the PCT value is obtained, which is directly proportional to the emission time of the signal.

EXAMPLE 2

Measuring Urinary Procalcitonin

The urine sample is taken using a syringe from the appropriate drainage site of the urinary catheter after clamping of the outflow and disinfection. About 4 mL of urine is transferred into the appropriate tube to be transported to the analysis laboratory. The determination of the urinary PCT once the sample was taken was performed according to the protocol provided for plasma PCT, as described in Example 1.

Bibliography

Hooton T M et al. Diagnosis, prevention, and treatment of catheter-associated urinary tract infection in adults: 2009 International Clinical Practice Guidelines from the Infectious Diseases Society of America. Clin Infect Dis. 2010 Mar. 1; 50(5):625-63.

The invention claimed is:

1. An in vitro method for diagnosis and/or monitoring of the presence of a urinary tract infection (UTI) in a subject who does not have renal dysfunction, and who has symptoms of and is suspected of having a UTI, or who was previously diagnosed as having a UTI, comprising
   (a) detecting and quantitating the concentration of procalcitonin (PCT) in a urine sample from the subject and in a plasma sample from the subject, wherein the detection and quantitation comprises a PCT detection assay wherein the sample is contacted with an antibody that specifically binds to PCT to form a detectable PCT: antibody complex, and detecting and quantitating the complex;
   (b) comparing the detected concentration of PCT in the subject's urine sample with the concentration of PCT in the subject's plasma sample, wherein a ratio between the PCT concentration in the urine sample and the PCT concentration in the plasma sample>1 is predictive of the presence of the UTI; and
whereby the diagnosis or monitoring of the presence of the UTI is used to determine whether to prescribe a UTI treatment for the subject, when the subject being diagnosed or monitored is predicted to have or still have the UTI.

2. The method of claim 1, wherein procalcitonin concentration is determined by a primary antibody specific for the procalcitonin.

3. The method of claim 2, wherein said primary antibody is directly labeled with a fluorochrome selected from the group consisting of: hydroxycoumarin, aminocoumarin, methoxycoumarin, Europium, Samarium, FITC, Cy3, Cy5, Cy2, Cy7, and XL665.

4. The method of claim 2, wherein procalcitonin concentration is determined by a secondary antibody labeled with a compound selected from the group consisting of: hydroxycoumarin, aminocoumarin, methoxycoumarin, Europium, Samarium, FITC, Cy3, Cy5, Cy2, Cy7, and XL665.

5. The method of claim 4 wherein said secondary antibody is specific for said primary antibody.

6. The method of claim 1, wherein said urinary tract infection is associated with urinary catheter use.

* * * * *